(12) United States Patent
Larsen et al.

(10) Patent No.: US 9,211,069 B2
(45) Date of Patent: Dec. 15, 2015

(54) PERSONAL PROTECTIVE EQUIPMENT WITH INTEGRATED PHYSIOLOGICAL MONITORING

(75) Inventors: Christopher Scott Larsen, Rockford, MN (US); Aravind Padmanabhan, Plymouth, MN (US); Christopher Humphrey, San Diego, CA (US); Neal Muggleton, Trondheim (NO)

(73) Assignee: Honeywell International Inc., Morristown, NJ (US)

( * ) Notice: Subject to any disclaimer, the term of this patent is extended or adjusted under 35 U.S.C. 154(b) by 678 days.

(21) Appl. No.: 13/399,747

(22) Filed: Feb. 17, 2012

(65) Prior Publication Data

US 2013/0218022 A1 Aug. 22, 2013

(51) Int. Cl.
*A61B 5/00* (2006.01)
*A61B 5/01* (2006.01)

(52) U.S. Cl.
CPC *A61B 5/01* (2013.01); *A61B 5/6817* (2013.01)

(58) Field of Classification Search
CPC ..................................................... A61B 5/6817
USPC .......................................................... 600/474
See application file for complete search history.

(56) References Cited

U.S. PATENT DOCUMENTS

| | | | |
|---|---|---|---|
| 4,510,812 A * | 4/1985 | Feng | 73/644 |
| 5,062,432 A | 11/1991 | James et al. | |
| 5,879,294 A * | 3/1999 | Anderson et al. | 600/310 |
| 6,556,852 B1 * | 4/2003 | Schulze et al. | 600/323 |
| 7,209,775 B2 * | 4/2007 | Bae et al. | 600/340 |
| 7,625,117 B2 | 12/2009 | Haslett | |
| 7,985,468 B1 * | 7/2011 | Gilder et al. | 428/317.9 |
| 2005/0283081 A1 | 12/2005 | Lin et al. | |
| 2007/0106172 A1 | 5/2007 | Abreu | |
| 2007/0147635 A1 * | 6/2007 | Dijkstra et al. | 381/94.1 |
| 2007/0177651 A1 | 8/2007 | Daugherty et al. | |
| 2008/0146890 A1 * | 6/2008 | LeBoeuf et al. | 600/300 |
| 2008/0154098 A1 | 6/2008 | Morris et al. | |
| 2009/0036744 A1 * | 2/2009 | Vayser | 600/182 |
| 2009/0105605 A1 | 4/2009 | Abreu | |
| 2009/0199317 A1 | 8/2009 | Schwiers | |
| 2009/0221884 A1 | 9/2009 | Ryan | |
| 2009/0221888 A1 | 9/2009 | Wijesiriwardana | |
| 2010/0113894 A1 | 5/2010 | Padiy | |

(Continued)

FOREIGN PATENT DOCUMENTS

| | | | | |
|---|---|---|---|---|
| WO | WO2007/004083 | * | 1/2007 | A61B 5/02 |
| WO | 2009091657 A1 | | 7/2009 | |
| WO | 2011127063 A1 | | 10/2011 | |

OTHER PUBLICATIONS http://www.omronhealthcare.com/products/3-series-wrist/; Nov. 8, 2011; 9 pages.

(Continued)

*Primary Examiner* — Tse Chen
*Assistant Examiner* — Patricia Park
(74) *Attorney, Agent, or Firm* — Conley Rose, P.C.; Kristin Jordan Harkins

(57) ABSTRACT

Embodiments may comprise personal protective equipment with integrated physiological monitoring. Some embodiments may relate specifically to in-ear devices (such as hearing protection and/or communication devices) having one or more physiological sensors for early monitoring for heat related illnesses. Several embodiments may incorporate a temperature sensor and a speaker into such in-ear device.

14 Claims, 6 Drawing Sheets

(56) References Cited

U.S. PATENT DOCUMENTS

| | | | | |
|---|---|---|---|---|
| 2010/0195860 | A1* | 8/2010 | Becker | 381/371 |
| 2010/0217100 | A1 | 8/2010 | LeBoeuf et al. | |
| 2010/0217102 | A1* | 8/2010 | LeBoeuf et al. | 600/310 |
| 2010/0307861 | A1* | 12/2010 | Tiemens | 181/135 |
| 2011/0106627 | A1 | 5/2011 | LeBoeuf et al. | |
| 2011/0257521 | A1* | 10/2011 | Fraden | 600/438 |

OTHER PUBLICATIONS http://sensewear.bodymedia.com/SW-Learn-More/Product-Overview; Introducing the Enhanced BodyMedia SenseWear System; Nov. 8, 2011; 2 pages.

http://www.welch-allyn.com/apps/products/product.jsp?id=11-ac-100-0000000001196; 11-8-11; 1 page.

http:www//thoughttechnology.com/gsrtemp2x.htm; Nov. 8, 2011; 1 page.

http://www.nlm.nih.gov/medlineplus/heatillness.html; Nov. 8, 2011; 4 pages.

http://ehs.okstate.edu/kopykit/HEAT.HTM; OSU EHS Safety Training, Heat Stress, Nov. 8, 2011; 2 pages.

http://www.questtechnologies.com/ProductCategory/Heat-Stress-Monitors_6.aspx; Nov. 8, 2011; 2 pages.

http://www.drgreene.com/azguide/heat-stroke; Nov. 8, 2011; 1 page.

http://www.revolutionhealth.com/articles/heat-tetany/tw9489; Nov. 8, 2011; 1 page.

http://qubitsystems.com/human/s220-gsr-sensor/; Nov. 8, 2011; 5 pages.

McCombie, Devin Barnett; "Development of a wearable blood pressure monitor using adaptive calibration of peripheral pulse transit time measurements"; http://dspace.mit.edu/handle/1721.1145335; Nov. 8, 2011; 3 pages (Abstract).

Chon, K. H. et al.; "Estimation of respiratory rate from photoplethysmogram data using time-frequency spectral estimation"; http://www.ncbi.nlm.nih.gov/pubmed119369147; Nov. 8, 2011; 1 page.

Man, Jill Li Shing, "Usability of a Wireless Temporal Artery Bandage Thermometer"; Thesis, Mar. 2008, Department of Mechanical and Industrial Engineering, University of Toronto, 98 pages.

http://www.mayoclinic.com/health/first-aid-heat-stroke/FA00019; Nov. 8, 2011; 2 pages.

http://www.mayoclinic.com/health/first-aid-heat-exhaustion-/FA00020; Nov. 8, 2011; 2 pages.

Muir, I. H. et al.; "Prediction of rectal temperature from ear canal temperature"; Ergonomics ISSN 0014-0139, 2001, vol. 44, No. 11, pp. 962-972.

Payne, R.A., et al.; "Pulse transit time measured from the ECG: an unreliable marker of beat-to-beat blood pressure"; 2006 the American Physiological Society; http://www.jap.org; Journal of Applied Physiology; vol. 100; pp. 136-141.

http://www.generaltools.com/SAM800IND--DIGITAL-POCKET-HEAT-INDEX-MONIT . . . ; Nov. 8, 2011; 2 pages.

Hey; Stefan, et al.; "Continuous noninvasive Pulse Transit Time Measurement for Psycho-physiological Stress Monitoring"; University of Karlsruhe; 4 pages.

http://stresseraser.com/pdfs/publications; Nov. 8, 2011; 10 pages.

http://www.welch-allyn.com/apps/products/product.jsp?id=11-ac-100-0000000001198; Nov. 8, 2011; 1 page.

http://www.bom.gov.au/info/thermal_stress/; Australian Government Bureau of Meterology, Thermal Comfort observations; Nov. 8, 2011; 7 pages.

http://www.generaltools.com/-WBGT8758--Deluxe-Heat-Index-Monitor_p_698.html; Nov. 8, 2011; 2 pages.

Walsh, Michael et al.; "The Smart Helmet: A Practical Demonstration of Smart Environments in Sports"; Centre for Adaptive Wireless Systems; Department of Electronic Engineering; Cork Institute of Technology; Bishopstown, Cork, Ireland, pp. 129-134.

Chiang, Jeff et al.; "The Heat Elite"; Business Proposal: The ThermaTracker, Columbia University, School of Engineering and Applied Science, Biomedical Engineering Senior Design, Fall 2008, 10 pages.

\* cited by examiner

PERSONAL PROTECTIVE EQUIPMENT WITH INTEGRATED PHYSIOLOGICAL MONITORING

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments may relate generally to personal protective devices having one or more integrated physiological sensors for monitoring a worker's health parameters, and more specifically to devices for early monitoring for heat-related illness which may be incorporated into personal protective equipment that a worker already wears.

BACKGROUND

People working in hot environments are often particularly susceptible to heat related illnesses, such as heat exhaustion and heat stroke. For example, first responders (such as firefighters and police officers, for example), soldiers, athletes (such as football players, for example) and other workers (such as foundry workers, welders, and road construction crews, for example) may work in stressful and/or hot conditions. And protective gear worn by such workers may add to the heat and physical stress concerns. Heat-related illnesses are of real concern in such instances, and can result in hospitalization or even death. For example, heat stroke can have fatality rates as high as 50%. Thus, it may prove useful to employ some sort of regular or continuous monitoring of worker physiological parameters, to allow for early detection of the signs of heat-related illness or other stresses before the situation becomes serious. This type of monitoring may allow for preventative action to be taken early enough to prevent serious consequences. After all, once signs of heat stroke become readily apparent based on casual observation, it might well already be too late to avoid serious health concerns.

And individual monitoring may prove most effective, since individuals can react to temperature and other stresses differently. Often the best warning indicator for heat-related illness may be body core temperature. By observing rising body core temperature (or some effective proxy for body core temperature), it may be possible to provide an early alert warning of potential heat-related illness in time to allow for preventative measures (such as removing the worker from the heat environment, providing medical evaluation and/or care, and/or providing cooling measures, for example). But to be effective, the monitoring may need to be capable of being performed in an unobtrusive manner, with the physiological parameter(s) being monitored in a way that is accurate, comfortable, and well-accepted by the workers in order to improve compliance. This is particularly true if the monitoring is to be fairly continuous over a long duration (such as a work shift). Applicants therefore have developed embodiments of personal protective equipment that have integrated physiological sensors incorporated therein, as described in more detail below.

SUMMARY

Aspects of the disclosure may include embodiments of a device comprising one or more of the following elements and/or features in any combination: an earpiece for use in a user's ear having a sealing ear tip, a main body, and a stem; at least one temperature sensor (typically located within the main body); a speaker (typically located within the main body) having a face; a sound waveguide; an IR waveguide; wherein: the stem is elongate and has a front and a rear; the stem has a length sufficient that, when the device is in place in the user's ear, the stem extends forward from the main body past at least a first bend of the user's ear canal; the stem is sufficiently flexible to comfortably conform to curvature of the users ear canal; the main body is shaped to fit in the bowl of the user's ear and has a front; the rear of the stem is securely attached to the front of the main body; the sealing ear tip comprises polyurethane foam sufficiently pliable to form a good seal in the user's ear canal and is securely attached about the front of the stem; the temperature sensor comprises an IR thermometry sensor having a face; the speaker and the sensor are located in the main body near the rear of the device; the sound waveguide extends from the speaker face, through the length of the stem, forward to the front of the stem; the sound waveguide comprises an inner surface that is substantially sound reflective (typically with less than 6 dB attenuation); the IR waveguide extends from the IR sensor face, through the length of the stem, forward to the front of the stem; the IR waveguide is substantially transmissive of IR waves; the IR waveguide and the sound waveguide each comprise at least one curve; the waveguides function despite any additional curvature arising when the earpiece is inserted into the user's ear canal; and the IR waveguide extending past at least the first bend may provide alignment of the IR sensor towards the user's tympanic membrane (When the device is inserted into the user's ear canal). In some embodiments, the IR waveguide may comprise an elongate hollow tube; and the IR waveguide may have an inner surface that is reflective of IR (typically for spectrally flat transmission). In some embodiments, the IR waveguide may comprise a mirrored inner surface of polished metal. In alternative embodiments, the IR waveguide may comprise a fiber-optic cable. In some embodiments, the stem has a length between about 12-20 mm and/or between about 18-20 mm. In some embodiments the device may further comprise at least one secondary physiological sensor and a controller, wherein the controller uses the secondary physiological sensor as verification of the temperature sensor to determine heat-related illness desigiation. And in some embodiments, a single y-shaped waveguide may serve as both the sound waveguide and the IR waveguide, with one branch attaching to the speaker face and one branch attaching to the IR sensor face.

In other aspects, the disclosure may include embodiments of a device comprising one or more of the following elements and/or features in any combination: an earpiece for use in a user's ear having a sealing ear tip; at least one temperature sensor; a speaker having a face; and one or more waveguides; wherein: the earpiece has a length sufficient so that when in place in the user's ear it extends forward past at least a first bend of the user's ear canal; the sealing tip is sufficiently pliable to form a good seal in the user's ear canal. In some embodiments, the temperature sensor may comprise a thermistor; and the ear tip may comprise polyurethane foam. In other embodiments, the temperature sensor may comprise an IR sensor. In some embodiments, the one or more waveguides may comprise a sound waveguide and an IR waveguide; wherein the sound waveguide comprises an elongate hollow tube extending from the speaker face forward so that, when in place in the user's ear, the sound waveguide directs sound produced by the speaker into the user's ear canal at a point past the sealing ear tip; and wherein the sound waveguide comprises an inner surface that is substantially sound reflective. In some embodiments, the IR waveguide may comprise a fiber-optic cable, in some embodiments, the IR waveguide may comprise an elongate hollow tube having an inner surface that is substantially reflective of IR which extends from the face of the IR sensor forward so that, when in place in the user's ear, the IR waveguide allows the IR sensor to detect the temperature in the ear canal. And in some embodiments, a single waveguide may function as both a sound waveguide for the speaker and an IR waveguide for the IR sensor, with the single waveguide having an inner surface that is reflective of both sound and IR. In some embodiments, the device may further comprise at least one secondary physiological sensor for verification of heat related illness detected by the temperature sensor. In some embodiments, the device may further comprise a helmet having a headband comprising one or more secondary physiological sensors for verification of heat-related illness. And some embodiments may further comprise an armband having one or more secondary physiological sensors for verification of heat-related illness.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
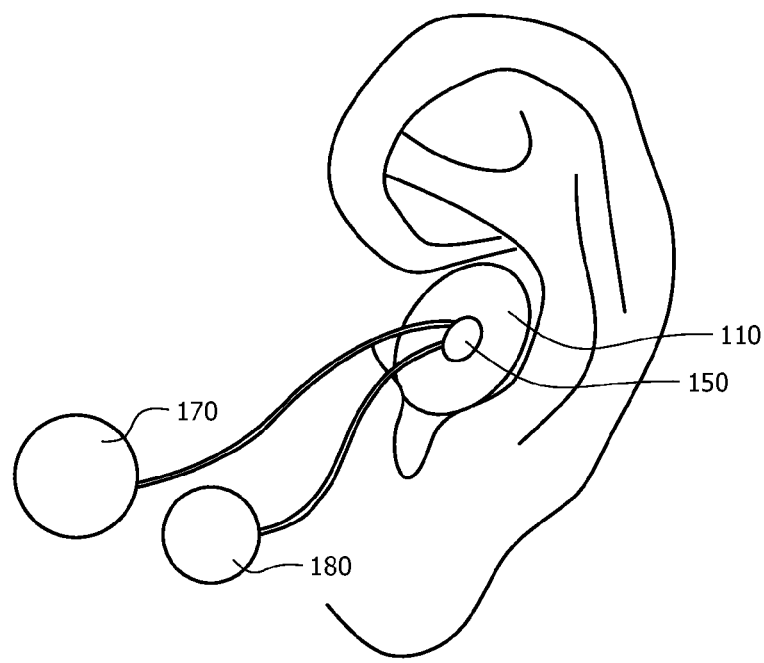
FIG. 1 illustrates a schematic of an in-ear embodiment.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "EarTip" generally refers to either an ear tip for use on a sound transmission device (such as an earbud for a communication headset, a hearing aid, or a portable music device, by way of non-exclusive example), to an earplug for protecting the user's hearing, or to any device comprising such ear tip or earplug elements, with the EarTip typically comprising a resilient portion designed to fit snugly in a user's ear canal; while this disclosure typically describes embodiments directed to ear tips, it should be understood that the disclosure is broad enough to include any sort of EarTip;

The term "foam" generally refers to a foam material with resilient recovery properties; foam materials may be low resilient and have slow recovery properties, such that if the foam is compressed and then released, the foam returns back towards its original uncompressed state over a period of time (typically greater than 10 seconds but less than 30 minutes, for example); or foam materials may be resilient and have moderate to fast recovery properties, such that they do not take a long-term set but return back towards the original uncompressed state fairly quickly (typically less than 10 seconds, for example); foam materials may be viscoelastic, and one example of such a viscoelastic foam plastic might be latex-modified polyurethane foam;

The term "sound transmission device" generally refers to any device for transmitting sound into a user's ear canal from an outside source, and by way of nonexclusive example may include personal music devices (such as an IPod™), a communication headset or earpiece, or a hearing aid;

The terms "front" and "rear" are used as relative descriptions of the opposing ends of an EarTip, with "front" typically describing the end that is directed towards and closest to the ear drum when the EarTip is inserted in a user's ear canal, and "rear" typically describing the end that is directed outward, away from, and furthest from the ear drum;

The terms "inner" and "outer" are relative descriptions describing locations based on their location within the ear canal (and/or their location when an EarTip is located within a user's ear canal), with "inner" relating to a direction closest to the ear drum and/or tympanic membrane and "outer" relating to a direction away from the ear drum and/or tympanic membrane;

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments relate generally to personal protection equipment having one or more integrated physiological sensors. The sensors are typically integrated into the personal protection equipment ("PPE") in a way that may allow monitoring to take place unobtrusively, without any noticeable difference to the user/worker (who is already accustomed to wearing such personal protective equipment anyway). In other words, embodiments typically may seek to incorporate the sensor(s) into the PPE so that physiological parameters may be monitored on an individual basis when the PPE is used in its customary manner (with little or no added steps or extraneous equipment (noticeable or apparent to the user beyond the confines of the PPE) needed to allow the PPE to operate as normal while also providing monitoring of physiological parameters). Other embodiments may have sensors that require some extraneous equipment (that might not be entirely contained within the PPE), but preferably seek to minimize it to encourage compliance.

Often, embodiments may be particularly interested in monitoring core body temperature (or a reliable proxy for core body temperature), in order to provide early warning of possible heat-related illnesses. For example, a body core temperature of about 40.6 degrees Celsius or higher might indicate that there is a risk of heat-related illness (and the earlier the rising body core temperature can be detected, the better chance to prevent heat-related illness). One or more temperature sensors would typically be incorporated into a PPE device to allow for unobtrusive monitoring of body core temperature. Optionally, additional physiological sensors might also be incorporated into the PPE device as secondary sensors, typically used as a check on the primary temperature data to reduce the chance of false warnings. So for example, if the primary temperature sensor indicates that there is no risk of heat-related illness (i.e. the user's body core temperature is within acceptable limits), but the one or more secondary sensors provide contra-indicating data that suggest there could be a problem, a warning could be given (to address false-negative concerns in the interest of being overly rather than under inclusive when health may be at stake). Or for example, if the primary temperature sensor indicates that there is a risk of heat-related illness (i.e. the user's body core temperature is outside the acceptable limits and/or has entered a warning or danger zone), but multiple secondary sensors provide contra-indicating data that suggests that there is no physiological problem, a warning override might apply to prevent false-positive warnings (or alternatively, the warning might still be issued but include a flag that allows the user or other person monitoring the data to make a more informed decision). Secondary sensors night, for example, detect perspiration (sweat) rate, pulse or heart rate, pulse oxygen saturation, respiration (breath) rate, ECG or EKG, and/or blood pressure.

Since heat-related illnesses tend to produce multiple physiological responses, such secondary sensors might provide useful information to assist in evaluating the temperature data in determining if a warning should be issued. For example, the following physiological responses might be indicative of heat-related illness: rapid heart rate, rapid breathing, heavy sweating (or alternatively no sweating in the case of heat stroke), and/or weak pulse. Thus, some embodiments may incorporate one or more secondary sensors into the PPE, in addition to (or even perhaps instead of) one or more temperature sensors.

While one or more physiological sensors might be incorporated into any type of PPE device, specific embodiments might include an in-ear PPE device (which might be an earplug or other hearing protection device or a communication headset, for example), a helmet PPE device (with the sensors typically integrated into the headband of a protective helmet, such as a fire helmet, for example), and/or an armband device (which might, for example, be incorporated into a protective coat such as a turnout coat or gear). FIG. 1, for example, shows an exemplary embodiment having a temperature sensor 150 incorporated into an EarTip 110 (which might for example be an earplug or other hearing protection device and/or an ear tip for a communication device or other sound transmission device). This embodiment might be particularly useful for workers who already wear one or more EarTips as part of their jobs (since it may help to ensure compliance without any cumbersome additional steps or equipment). The embodiment of FIG. 1 has the temperature sensor 150 mounted entirely within the EarTip 110, and also has a galvanic skin response (GSR) 180 sensor with at least one conductive electrode extending out from the EarTip 110 (so that it might be attached to the user's skin, for example on the user's neck using an adhesive), and a pulse oximeter sensor 170 extending out from the EarTip 110 (so that it might be attached to the user's earlobe for example).

Figure 2:
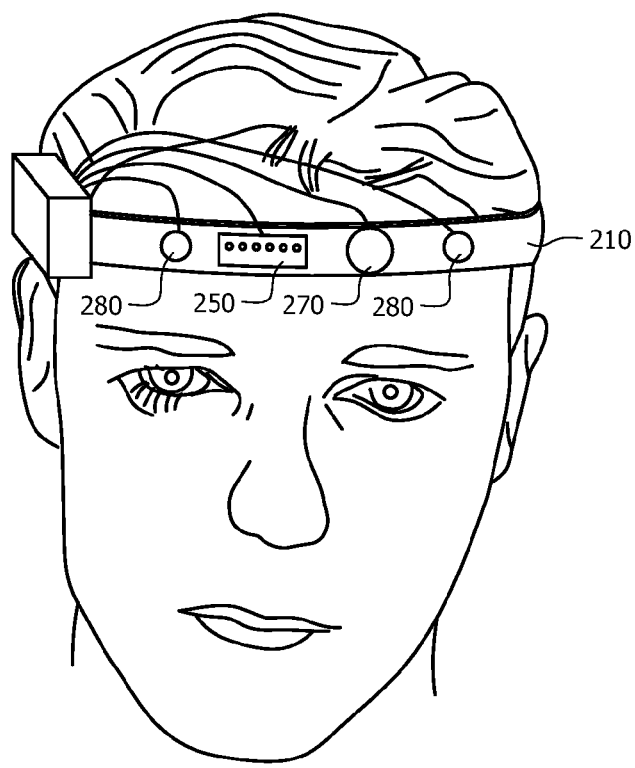
FIG. 2 illustrates a schematic of a headband embodiment (of the sort that might be used in a helmet)
Figure 3:
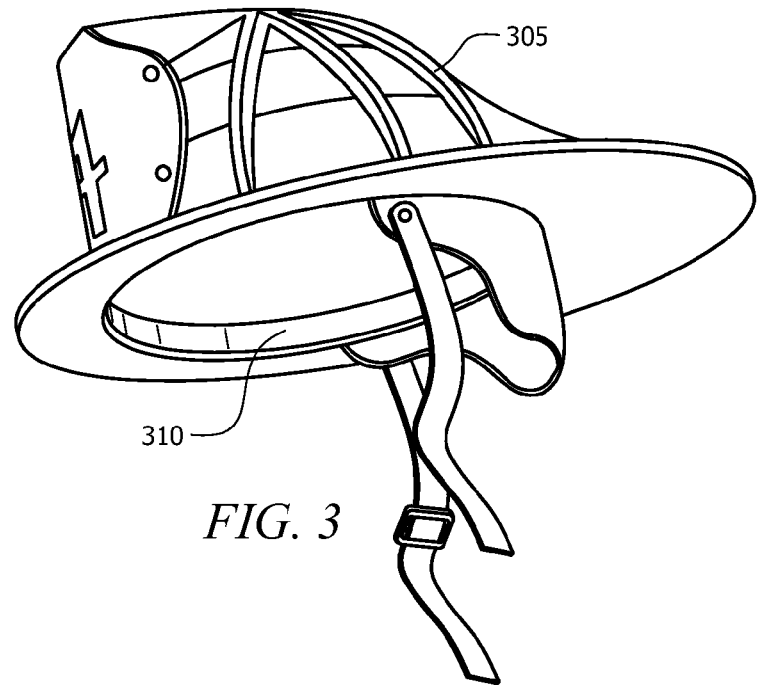
FIG. 3 illustrates a perspective view of a helmet having a headband similar to that of FIG. 2.

FIG. 2, on the other hand, illustrates an exemplary embodiment having a temperature sensor 250 (which might for example be a temporal artery thermistor array) incorporated into a headband 210 (typically a headband mounted into a protective helmet for example). Protective helmets often have a headband allowing the helmet to be sized to fit the user's head securely and/or to hold the hard shell of the helmet away from direct contact with the user's head. So the headband 210 of FIG. 2 might be mounted within the protective shell of the helmet such as shown in FIG. 3, for example, having a headband 310 and a protective helmet shell 305), so that one or more of the user's physiological parameters (such as core temperature) might be monitored automatically whenever the user is wearing the helmet. This may allow for unobtrusive monitoring without the need for the user to perform any additional steps or wear any extraneous equipment that might be cumbersome or unwieldy. The embodiment of FIG. 2 may also have additional, secondary sensors incorporated. For example, the embodiment of FIG. 2 may have a pulse oxygen sensor 270 and/or a GSR sensor 280 (which may have two or more conductive electrodes). So the headband embodiment of FIG. 2 might allow for unobtrusive monitoring of multiple physiological parameters whenever the helmet is worn.

Figure 4:
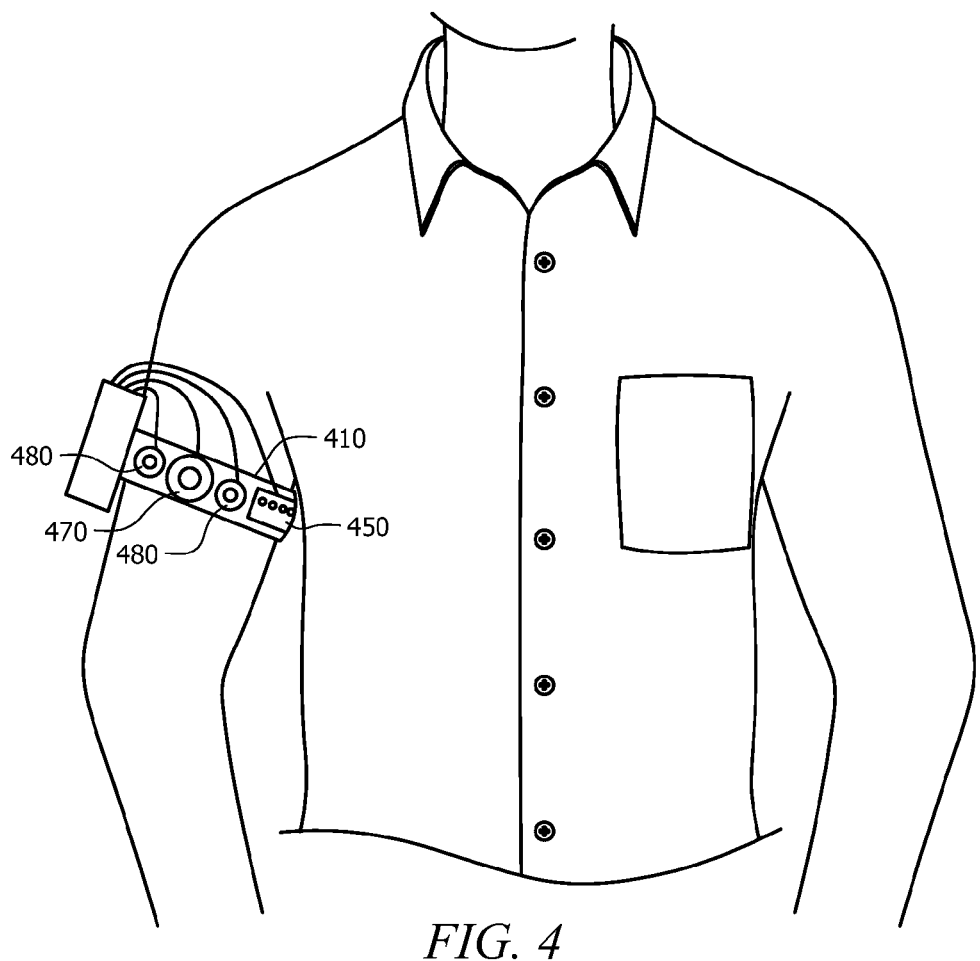
FIG. 4 illustrates a schematic of an armband embodiment.

FIG. 4 shows another illustrative embodiment having a temperature sensor 450 incorporated into an armband 410. The armband 410 might be incorporated into a protective coat, suit, or other turn-out gear (including firemen's coats and/or hazmat type suits), and typically would be located so that the temperature sensor 450 might be located in the user's armpit area (or some other position located for effective temperature measurement). In some embodiments, the armband 410 might be an elastic material secured within the inside surface of an arm or sleeve of the coat or protective suit (perhaps using a chassis system so that an armband of smaller diameter is held within the sleeve, typically towards the center of the sleeve), to provide snug and secure contact of the one or more physiological sensors to the user. Typically, the armband 410 would have a smaller diameter than the sleeve of the PPE and would be positioned and secured to the inside of the sleeve so that when the PPE is donned in ordinary fashion, the armband fits snuggly on the user's arm. Typically the armband is elastic (stretchable) and is sized so that it is smaller than the expected user's arm to ensure a snug, but not too tight, fit. So, one or more of the user's physiological parameters (such as core temperature) might be monitored automatically whenever the user is wearing the coat, suit, or other gear with the armband 410. This may allow for unobtrusive monitoring without the need for the user to perform any additional steps or wear any extraneous equipment that might be cumbersome or unwieldy. The embodiment of FIG. 4 may also have additional, secondary sensors incorporated. For example, the embodiment of FIG. 4 may have a pulse oxygen sensor 470 and a GSR sensor 480 (which may have two or more conductive electrodes). So the armband embodiment of FIG. 4 might allow for unobtrusive monitoring of multiple physiological parameters whenever the armband is worn.

In some embodiments, one or more physiological sensors might be mounted in one type of PPE, while another one or more physiological sensors might be mounted separately into another type of PPE. This type of arrangement might be most useful if the worker typically already wears multiple PPE as part of the job (so that it would not require any additional steps or extraneous gear). In such an arrangement, the sensors from the multiple PPE devices might all be monitored and/or operated using a single control device. One possible benefit of this approach would be that the sensors might be mounted in a way that minimizes disruption or unwieldiness. For example, mounting secondary sensors in an EarTip may not be as convenient, since it might require sensor elements to extend out beyond the EarTip. So it might be possible to have a temperature sensor mounted within an EarTip, for example, and to have one or more secondary sensors (or even another temperature sensor) mounted in another PPE device (such as a helmet headband or armband of a turnout coat, for example). The data from all the physiological sensors might then be analyzed by a processor in a single controller to determine if a warning is appropriate.

Typically, temperature sensors might comprise one or more thermistors (or even an array of thermistors lined across an artery such as the temporal artery in some embodiments), a scanning infrared sensor (such as an IR temperature sensor), a skin temperature thermometer, or other thermometry device. Pulse rate might be sensed using a (transmissive or reflective) pulse oximeter sensor, and this sensor could also be used to provide pulse oxygen saturation and perhaps thereby respiration rate (by using the pulse oximeter data and considering envelope modulation of its plethysmograph). Perspiration (sweat) rate might be determined by galvanic skin response, typically using conductive electrodes. Conductive electrodes (perhaps the same ones used for galvanic skin response in some embodiments) might also be used to monitor ECG (which can then be compared to the plethysmograph heart timing to derive the pulse transit time, from which blood pressure may be inferred). A delay between the electrical pulse of the heart (from the ECG) and the plethysmograph pulse may indicate an increase in blood pressure, for example. One or more of these physiological sensors might be incorporated in PPE.

Since body core temperature (or an effective proxy) may be the best indicator of heat related illness, at least one temperature sensor may be used as the primary sensor (with other, secondary sensors used primarily to identify likely false alarms—serving as false positive/negative verification). In other embodiments, however, one or more other sensors might be used as the primary sensor, either alone or in combination. Typically, temperature measurements from the temperature sensor might be correlated to actual body core temperature using a standard offset, for example. The use of an effective offset may allow other temperature measurements to be an effective proxy for body temperature. By way of example, the offset might be determined by performing series of tests, in which test subjects are monitored using the desired thermometry device (such as a thermistor and/or IR sensor) while simultaneously being monitored for actual body core temperature (rectally, for example). Typically, a number of test subjects would be monitored for a period of time, perhaps while walking on a treadmill. For example, about 25 test subjects might be monitored for about 30-60 minutes while walking on a treadmill at approximately 80% of their maximum heart rate. At least 50 matching temperature measurements (using the preferred thermometry device and the body core sensing device, such as rectal thermometer) might be taken from each test subject. This data could then be correlated to determine a standard offset (which might then be used to correlate the temperature measurement using the preferred thermometry device to core body temperature. Alternatively, the offset could be personalized to each specific user by performing this type of test on each individual user. While this individualized testing might provide some accuracy benefits (by providing a customized offset), its level of inconvenience and discomfort would make most users prefer to use an average offset instead.

In the EarTip embodiment of FIG. 1, the thermometry device 150 would typically be either a thermistor or an IR sensor. To improve the operation of the thermistor in measuring the ear canal temperature, the ear canal typically should be well sealed and/or insulated (to prevent infiltration of external air from the ambient environment that might influence the temperature reading in the ear canal). This may be accomplished by having an effective sealing element for the EarTip. Typically, the sealing element might be an ear tip formed of foam, molded silicone, or other resilient materials. By way of example, the ear tip might be formed of polyurethane foam. The foam ear tip might have a shape that is generally a snub (flat) nosed bullet.

The foam ear tip of FIG. 1 would typically be located about a sound tube or other stem. The stem would be of a more rigid material than the foam (to aid in insertion), but would still be sufficiently pliable and/or flexible to allow it to conform to the irregular shape of a user's ear canal (for example, being capable of bending to extend comfortably beyond at least the first bend of the user's ear canal (and possibly extending past the second bend of the user's ear canal in some instances)). Typically, the stem may be sufficiently flexible and conforming so that even when it extends past the first bend of the user's ear canal, it could be comfortably worn by the user for an extended period (for example a whole shift, perhaps 8 hours). The foam of FIG. 1 might, for example, be located at the end of the sound tube or stem. In some embodiments, the foam would extend from the front tip of the sound tube stem rearward for about half the sound tube's length up to about 76 percent of the sound tube's length. Typically, the sound tube might extend about 13 mm from the housing of the main body. In other embodiments, the sound tube might extend at least 12 mm from the main body. Typically, the foam ear tip would be between about 6 mm and about 10 mm in length. In the embodiment of FIG. 1, the foam might be located on the sound tube so that when positioned in the user's ear canal, the foam would be located at approximately the point where the ear canal crosses the skull (since this often provides the best acoustic seal, and may also provide better insulation). The sound tube or stem (having the foam thereon for sealing) often is significantly longer than pre-existing devices, extending past the first bend of the user's ear canal to a location short of the tympanic membrane. In some embodiment, the sound tube might extend past the second bend in the user's ear canal to a location short of the tympanic membrane. In embodiments using IR temperature sensing technology, this close positioning with respect to the tympanic membrane may allow for better IR sensing as well.

Alternatively, the tympanic membrane temperature could be sensed using a non-contact IR sensor, for example (of the type typically used for in-ear thermometry). Alignment and positioning of the IR sensor may be quite important in getting a good temperature measurement, however. There should be little or no external light influencing the IR sensor (ideally, no external light would contact the IR sensor surface or face), and the IR sensor should be directed at or towards the tympanic membrane (to get a good reading that may correlate well to body core temperature). The better the alignment of the sensor towards the tympanic membrane, the better the temperature reading is likely to be. And a good sealing element, like a foam ear tip, may also be helpful in securing the device with the sensor in place in the user's ear canal. If positioning and alignment are difficult within the PPE EarTip, an optical waveguide and/or fiber-optic cable might be used to direct the IR sensor towards the tympanic membrane. By using an IR waveguide to extend deeper into the ear canal (past at least the first bend in the ear canal, for example), the IR sensor should obtain better (for example, more accurate, more consistent, and/or more closely corresponding to body core temperature as a better proxy) temperature readings, perhaps by improving alignment (so that the IR sensor is directed towards the tympanic membrane) and/or reducing the distance between the sensor and the tympanic membrane.

Figure 5:
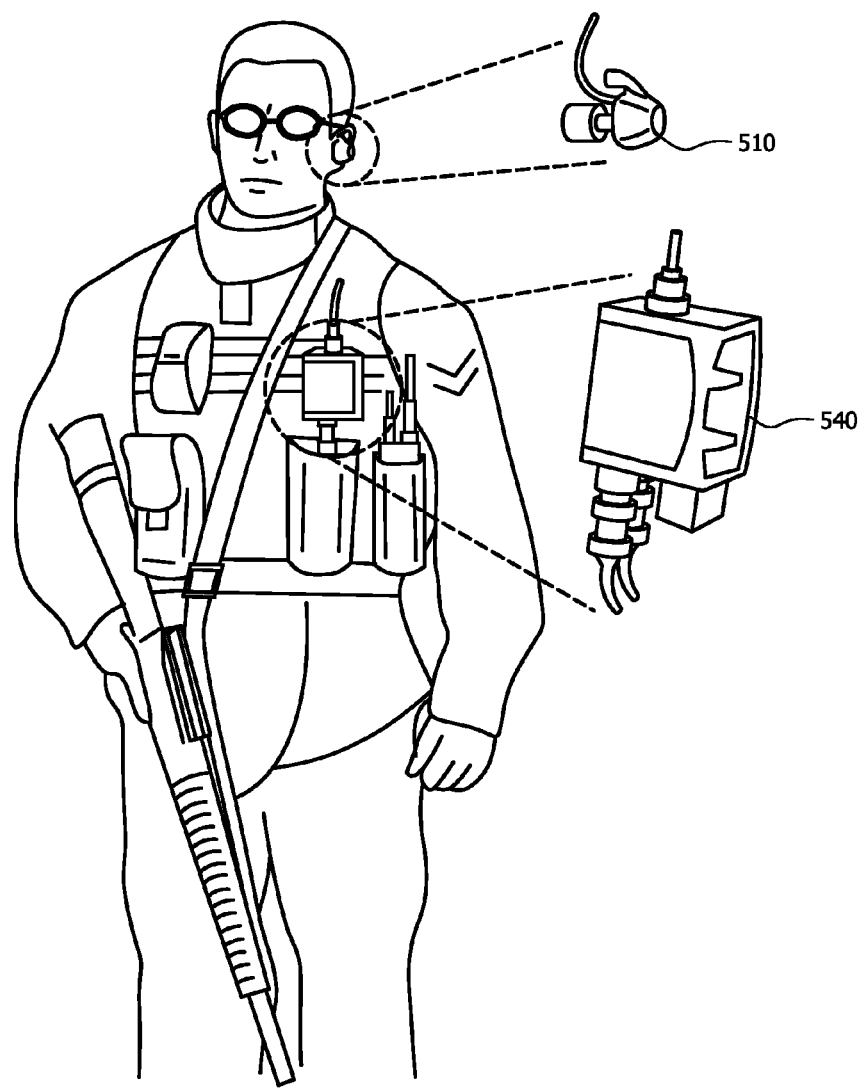
FIG. 5 illustrates a schematic of an in-ear system with an external controller.

FIG. 5 illustrates a particular headset device having an in-ear element (which may be a PPE device since it may also serve to provide hearing protection, passive and/or active). The system of FIG. 5 is an embodiment of a communication headset device, such as the QuietPro by Nacre AS. For further details about such sound transmission devices, please consult U.S. Pat. Nos. 6,728,385; 6,567,524; 6,661,901; 6,754,359; and 7,039,195 for example, which are hereby incorporated by reference for some embodiments herein to the extent that it is not inconsistent with and/or does not contradict information presented directly in the present disclosure. The embodiment of FIG. 5 comprises an in-ear headset 510 and a separate controller 540 (although in other embodiments, the control unit could be integrated into the in-ear headset).

FIGS. 6-10 illustrate various embodiments of in-ear headsets, of the sort that might be used for the QuietPro, for example. These embodiments are merely illustrative, and relate to headsets that incorporate at least an IR sensor and a speaker or other sound generator into the same in-ear headset earpiece. Other embodiments might use a thermistor as the thermometry device used with the speaker. Problematically, the limited amount of space in the sound tube of the in-ear headset (and/or the limited width of a user's ear canal) may make it difficult for both the speaker and the IR sensor to have access to the ear canal. Typically, both the speaker and the IR sensor are approximately 5 mm in diameter. Human ear canals typically range from about 5 to about 10 mm in diameter, such that there may be insufficient room for both elements to have unobstructed access to the ear canal. And both the speaker and the IR sensor typically need sufficient access to the ear canal to perform adequately. This space constraint may be overcome in some embodiments by using one or more waveguides (and in some embodiments, the IR sensor waveguide might be provided by a fiber-optic cable).

Figure 6:
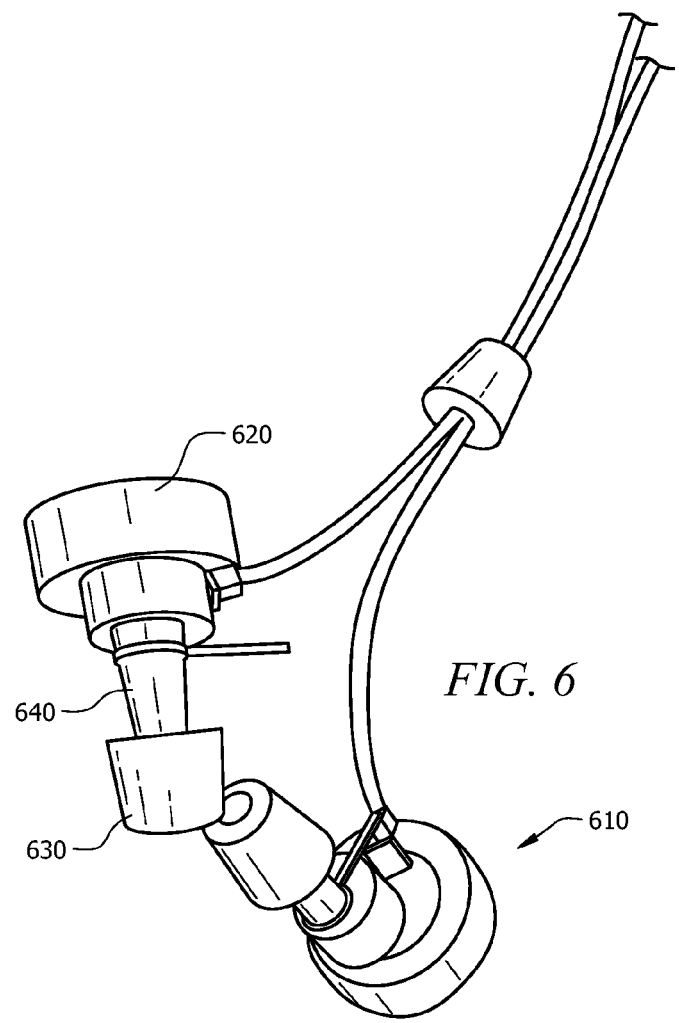
FIG. 6 illustrates a side elevation view of an embodiment of the in-ear headset of FIG. 5.

FIG. 6 illustrates an exemplary in-ear headset. The earpiece 610 comprises a main body 620 (which typically houses the electronic equipment, such as the speaker and IR thermometry sensor), a sound tube or stem 640 having a diameter or width smaller than the main body 620 and extending out forward from the front of the main body 620 (so that it may project deeper into the user's ear canal), and an ear tip 630 (typically operable to seal the user's ear canal, perhaps providing some level of hearing protection, and/or to secure the earpiece in place in the ear canal). Typically, the ear tip 630 would comprise an outer shape to fit securely within a user's ear canal in order to effectively seal the ear canal against passage of external sound from the external noise environment, and would be securely attached to the sound tube 640. While the attachment may be by means of glue or some other adhesive, in FIG. 6 a solvent-based adhesive may be used instead of glue, since the solvent tends to be less stiff than glue and may therefore improve comfort. The ear tip 630 is often shorter than the sound tube 640 and may often be located at the end of the sound tube 640 (such that the front end of the ear tip approximately corresponds to the front end of the sound tube (although the front of the sound tube may be inset slightly from the front end of the ear tip in some embodiments, so long as the ear tip design is effective to prevent the ear tip from occluding, partially or wholly, the sound tube). The ear tip 630 may be formed of any suitable foam material, and in the embodiment of FIG. 6 the ear tip is typically formed of polyurethane foam. The foam of the ear tip 630 typically has a foam density range of about 1.70e-05 to about 2.52e-05 g/cubic mm. The sound tube 640 is typically made of a material more rigid than that used for the foam body of the ear tip 630, but is nevertheless more flexible and/or pliable than a standard stem for a sound transmission device (since this may improve comfort, improve insertion, and/or provide a better fit by allowing the sound tube or stem to better conform to the user's ear canal). Typically, the sound tube 640 is sufficiently flexible or pliable to allow it to comfortably conform to the curvature of the user's ear canal, to allow for deeper insertion, better fit, and/or comfort. In the embodiment of FIG. 6, the sound tube 640 may have a hardness of about 65-85 Shore A and/or be formed of elastomeric polyurethane. In alternative embodiments, the sound tube might be formed of an alloy with TPE silicon.

The rear portion of the foam ear tip 630 of FIG. 6 may be undercut to provide an open rear annular space about the rear of the sound tube 640. In effect, the rear of the foam ear tip may include an integral rear flange (or skirt) that extends out rearward from the main body of the foam ear tip 630. The rear extension flange (or skirt) might include a periphery that encompasses the rear of the sound tube and the rear annular space (so that the rear of the sound tube is inset radially inward from the rear of the foam ear tip 630, forming the rear annular space between the sound tube and the rear extension flange of the ear tip). The rear annular space of FIG. 6 typically provides some space between the sound tube 640 and the extension flange (skirt) and encircles the sound tube 640, allowing the foam of the skirt to flex inward under application of external pressure. In the embodiment of FIG. 6, the rear extension flange may range in thickness from about 0.08-0.10 inches, and may have a length of about 0.20 inches. By incorporating the rear extension flange, the length of the ear tip may be extended up to about 0.690 inches (which is about a 75% increase over standard tip length) without substantially increasing perceived pressure in the user's ear canal. The ear tip of FIG. 6 has a length of about 0.69 inches. In this way, the rear extension flange may improve the seal for sound blocking and/or temperature insulation without significantly impacting comfort for long-term wear. And in some embodiments, the front of the foam ear tip may include a concave opening that provides access from the front of the sound tube into the user's ear canal (allowing the electronics in the main body housing 620 to have access to the user's ear canal when in place through the sound tube 640.

Figure 7:
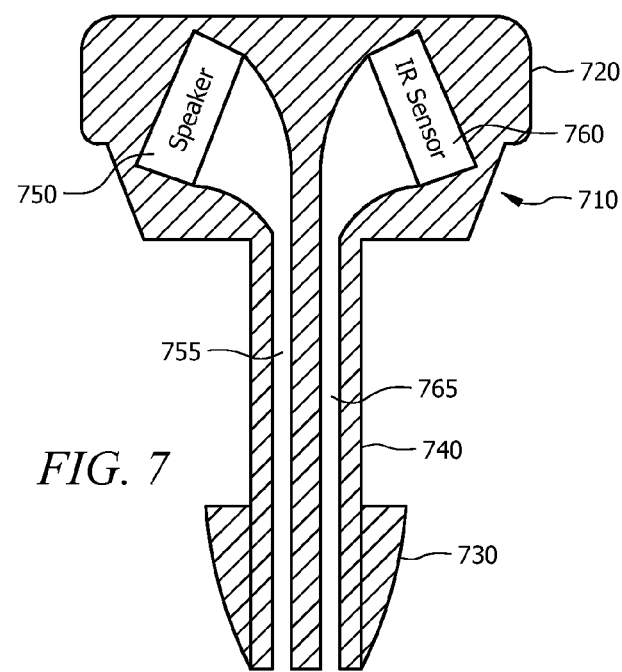
FIG. 7 illustrates a cross-sectional view of an embodiment of an in-ear headset device.

FIG. 7 shows an illustrative embodiment of such an earpiece 710. The ear piece 710 may comprise a speaker or other sound generator 750 and an IR thermometry sensor 760 (both typically located in the housing of the main body 720, which is typically designed to sit in the outer bowl of a user's ear). The speaker 750 is typically directed into the ear canal, for example directed towards the meatus, ear drum, and/or tympanic membrane, so that it might be used to transmit communication signals or other sound into the user's ear for example. A stem or sound tube 740 extends forward from the front of the main body 720, and an ear tip 730 is securely attached to the front end of the sound tube 740. The sound tube 740 of FIG. 7 may typically be an elongate tube, which may have one or more passages running its length. The one ore passages may comprise waveguides in some embodiments. The sound tube is typically sufficiently long so that when in place in a user's ear, it extends past at least the first bend in the user's ear canal (but not so far as to reach the user's tympanic membrane). In some embodiments, the sound tube might even extend past the second bend in the user's ear canal. In FIG. 7, the sound tube 740 may be about 12-13 mm long (and the main body housing 720 may be about 6-7 mm in length). In the embodiment of FIG. 7, the front of the sound tube 740 may extend about 12-20 ruin or about 18-20 mm into the user's ear canal, and typically the sound tube would be less than 20 mm in length (perhaps between 12-20 mm in length in some embodiments, for example). Typically, the sound tube is sufficiently stiff to allow for effective insertion of the ear tip 730 into the user's ear canal, but is also sufficiently flexible and/or pliable so that it may bend sufficiently to conform comfortably to the convolutions of the user's ear canal (allowing the sound tube to effectively navigate the first and/or second bends in the user's ear canal, for example). In other words, when the earpiece is inserted into a user's ear canal, the sound tube flexes and bends as needed to allow the ear tip to be inserted deeper into the user's ear canal, typically past at least the first bend of the ear canal. This flexibility may provide easier insertion and/or better comfort, and may allow the ear tip to be positioned deeper for a better seal.

The sound tube 740 of FIG. 7 may comprise one or more waveguides. In FIG. 7, the sound tube 740 comprises an acoustic (sound) waveguide 755 which may direct sound from the speaker 750 through the length of the sound tube (so that it may exit the sound tube and enter the user's ear canal). The sound tube 740 of FIG. 7 may also comprise an infrared (IR) waveguide 765 which may direct IR wavelengths effectively though the length of the sound tube 740, so that the IR thermometry sensor can more accurately measure the temperature of the tympanic membrane. In FIG. 7, the sound or speaker waveguide 755 may be a hollow tube of non-sound-absorbent material (typically having good sound reflectivity) extending from about the face of the speaker 750 through the length of the sound tube 740 and exiting out the front of the sound tube 740 (and/or the ear tip 730). Alternatively, the sound waveguide 755 may comprise an inner surface that is not sound absorbent, with the outer surface of the waveguide being some other material that provides sufficient support. Typically, the sound waveguide 755 may have less than about 6 dB attenuation. In some embodiments, the sound waveguide 755 may include one or more curves prior to insertion (with the reflective nature of the sound waveguide allowing sound to propagate effectively though the tube despite any one or more curvature). In FIG. 7, the sound waveguide 755 may be securely attached to the face of the speaker 750, and may flare at its rear end to encompass the face of the speaker 750. Use of the sound waveguide 755 may allow the speaker to be laterally offset from the sound tube 740 (so that the speaker face is not directly pointing towards the sound tube along a line that is parallel to the centerline of the sound tube). Additionally, the sound waveguide 755 may allow the speaker 750 to transmit sound effectively into the user's ear canal though an open passageway that is smaller than the width of the sound tube and/or speaker face (providing space for other waveguides and/or passages). In some embodiments, the sound waveguide may be sufficiently flexible so that it may bend as needed to allow the sound tube 740 to conform to the curvature of the user's ear canal (especially for insertion past at least the first bend of the user's ear canal). In some embodiments, insertion of the earpiece into the user's ear canal may result in additional curves in the sound waveguide, and the reflective nature of the waveguide may allow for effective transmission of sound from the speaker into the user's ear canal despite such curvature (allowing for the sound to enter the user's ear farther inward, closer to the ear drum).

The IR waveguide 765 of FIG. 7 may be a hollow tube of IR reflective material (for example, having low IR absorption). For example, the IR waveguide 765 might be a hollow tube having an inner surface of mirrored material, such as a polished metal inner surface. By way of example, the inner surface of the waveguide 765 might be aluminum or gold that is sufficiently polished to have good reflectivity of IR spectrum. Typically, the IR waveguide may provide spectrally flat transmission of IR and/or other heat radiating waves. The outer structure of the hollow tube IR waveguide might be made of any material that provides sufficient support and/or flexibility, so long as the inner surface is IR reflective. In some embodiments, the IR waveguide 765 may be sufficiently flexible so that it may bend as needed to allow the sound tube 740 to conform to the curvature of the user's ear canal (especially for insertion beyond at least the first bend of the user's ear canal). Alternatively, the IR waveguide 765 of FIG. 7 might comprise a fiber-optic cable for transmission of (typically at least long wave) IR. The IR waveguide 765 typically extends from about the front face of the IR sensor 760 through the length of the sound tube 740 and exiting the front of the sound tube (and/or ear tip 730), in some embodiments, the IR waveguide 765 may include curves (with the reflective nature of the IR waveguide allowing IR to propagate effectively though the tube despite any one or more curvature). In FIG. 7, the IR waveguide 765 may be securely attached to the IR sensor 760, and may flare at its rear end to encompass at least the face (sensor element) of the IR sensor 760 (so that little or no light or other IR sources would likely be detected by the IR sensor, in the hope of ensuring that the IR sensor provides accurate readings related to the temperature of the tympanic membrane within the user's ear canal). In fact, the flared rear end of the IR waveguide 765 could at least partially enwrap the IR sensor 760 in some embodiments. The flared rear end typically provides a smooth transition from the width of the IR sensor (or speaker) to the width of the smaller waveguide (for example, funneling the IR waves between the larger IR sensor face and the smaller waveguide main body diameter). Use of the IR waveguide 765 may allow the IR sensor 760 to be laterally offset from the sound tube 740. Additionally, the IR waveguide 765 may allow the IR sensor to effectively detect temperature in the user's ear canal though an open passageway that is smaller than the width of the IR sensor (providing space for other waveguides and/or passages). In some embodiments, the IR waveguide may be sufficiently flexible so that it may bend as needed to allow the sound tube 740 to conform to the curvature of the user's ear canal (especially for insertion past at least the first bend of the user's ear canal). In some embodiments, insertion of the earpiece into the user's ear canal may result in additional curves in the IR waveguide, and the reflective nature of the waveguide may allow for effective detection of temperature from the user's ear canal by the IR sensor despite such curvature.

While the embodiment specifically shown in FIG. 7 shows the IR waveguide 765 and the sound waveguide 755 running essentially parallel for most of their lengths (with centerlines that are parallel to the centerline of the sound tube 740), with only the rear portion of the waveguides 765 and 755 curving to orient with the corresponding device, in alternative embodiments the waveguides could include multiple curves. For example, the waveguides could curve around one another to be intertwined (such that each waveguide would be coiled). By using waveguides, the earpiece 710 may be able to use a thin sound tube 740 that does not have a width sufficient to allow side-by-side placement of the speaker 750 and IR sensor 760 (for example, because the width of the speaker plus the width of the IR sensor might be greater than the width or diameter of the sound tube). For example, the speaker face and IR sensor face might typically each be at least 5 mm in diameter. The waveguides, however, might each range in diameter from about 1 mm to about 3 mm in diameter (with fiber optic cable typically being even smaller than 1 mm in diameter). For the speaker, the largest waveguide width or diameter that will fit within the sound tube 740 along with the other waveguides might tend to perform better. So in one embodiment, the IR waveguide 765 would be a fiber-optic cable having a diameter of less than 1 mm, and most of the remaining width of the sound tube 740 would be devoted to the sound waveguide 755 (for example, up to the remaining width or diameter of the sound tube 740 absent structural support of the sound tube). Additionally, in some embodiments the waveguides might have additional curves once the earpiece (for example, the stem or sound tube) is inserted into the user's ear canal, as the sound tube bends to conform to the ear canal. The waveguides may allow for good readings and/or sound projection despite any curvature caused by insertion of the sound tube into the ear canal, and this may be particularly true if the waveguides have some degree of flexibility and/or if the waveguides have sufficient clearance in the sound tube to allow for sound tube flexing. In this way, the waveguides may allow for deeper insertion by addressing curvature issues that might arise when the stem extends past at least the first bend in the user's ear canal. And in some embodiments, the speaker and/or speaker waveguide may be optional, such that the embodiment might include only one waveguide (i.e. an IR waveguide for working with an IR sensor) within a stem (comfortably) extending past at least the first bend (typically to a point between about 12-20 mm or 18-20 mm within the ear canal) to provide alignment of the IR sensor so that it may be directed effectively at the tympanic membrane.

Figure 8:
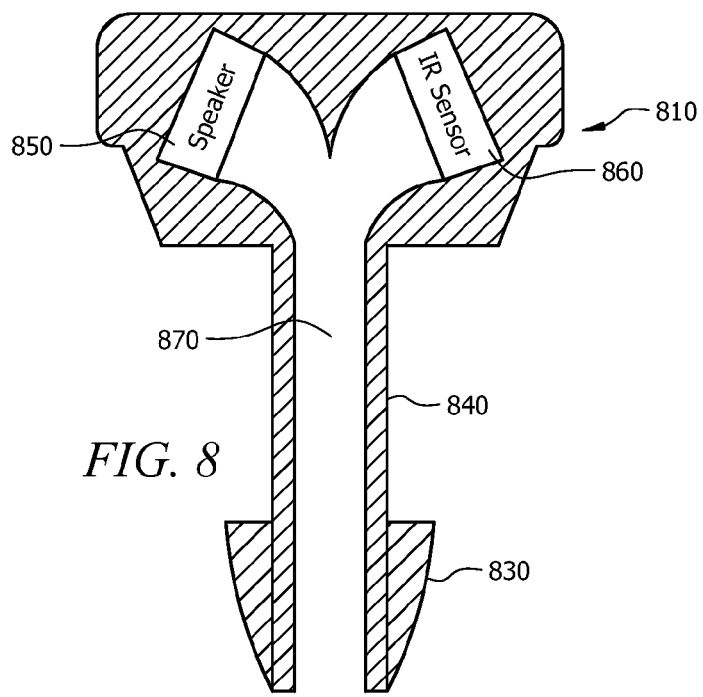
FIG. 8 illustrates a cross-sectional view of another embodiment of an in-ear headset device.

In the embodiment of the earpiece 810 as shown in FIG. 8, a single waveguide 870 might be used as the primary waveguide for both the speaker 850 and the IR sensor 860. Typically, the waveguide 870 would include a y-connector at its rear (with at least one sound waveguide branch directed towards the speaker 850 and typically having sound reflective properties, and one IR sensor waveguide branch directed towards the IR thermometry sensor 860 and typically having IR reflective properties). And the IR sensor 860 would typically be seated securely within a flared rear portion of one channel or branch of the y-shaped waveguide, to ensure that it would not be influenced by external factors. The main portion of the single y-shaped waveguide (typically the portion located within the sound tube) would typically be reflective of both sound and IR waves, so that the waveguide 870 might serve effectively as both a sound waveguide and an IR waveguide. For example, the main portion of the waveguide 870 might have at least an inner surface that is sound and IR reflective, for example a polished metal. And while both of the y-connector branches could also be both sound and IR reflective (and could be made for example of the same material as the main portion of the waveguide 870), in some embodiments each branch would only be reflective based on the electronic device at its rear (with the speaker branch being sound reflective and the IR sensor branch being IR reflective). The use of a single waveguide may allow for a wider waveguide main portion (for example, with a wider diameter), which may be particularly useful in maximizing sound transmission from the speaker deep into the ear canal. For example, the main portion of the waveguide 870 may take up most of the width of the stem or sound tube 840.

In some embodiments, the single waveguide might be used simultaneously for temperature measurements using the IR sensor and for sound projection from the speaker into the user's ear canal (typically past at least the first bend). In some such embodiments, the waveguide 870 might be secured within the sound tube 840 in a fashion that damps vibration (for example, the material of the sound tube might be an effective vibration damping material to minimize vibration within the waveguide). In other embodiments, for example, if the speaker produces too much vibration of the waveguide and might interfere with the IR sensor readings, the waveguide might be used in alternating fashion by the speaker and the temperature sensor (IR sensor) (so that, for example, the temperature measurement is only taken when there is no sound from the speaker in the waveguide). This could be accomplished by having an interrupt feature in the controller, which would only allow one electronic device in the earpiece to be used at a time (i.e. they could take turns). So for example, the speaker might be interrupted (temporarily prevented from transmitting sound) whenever the IR sensor is in use to allow for improve accuracy in the temperature reading. If a thermistor thermometry device is used instead of an IR sensor, then simultaneous measurements should work effectively (particularly if the vibrations from the speaker do not loosen the snug fit of the ear tip sealing element 830 within the user's ear canal).

Figure 9:
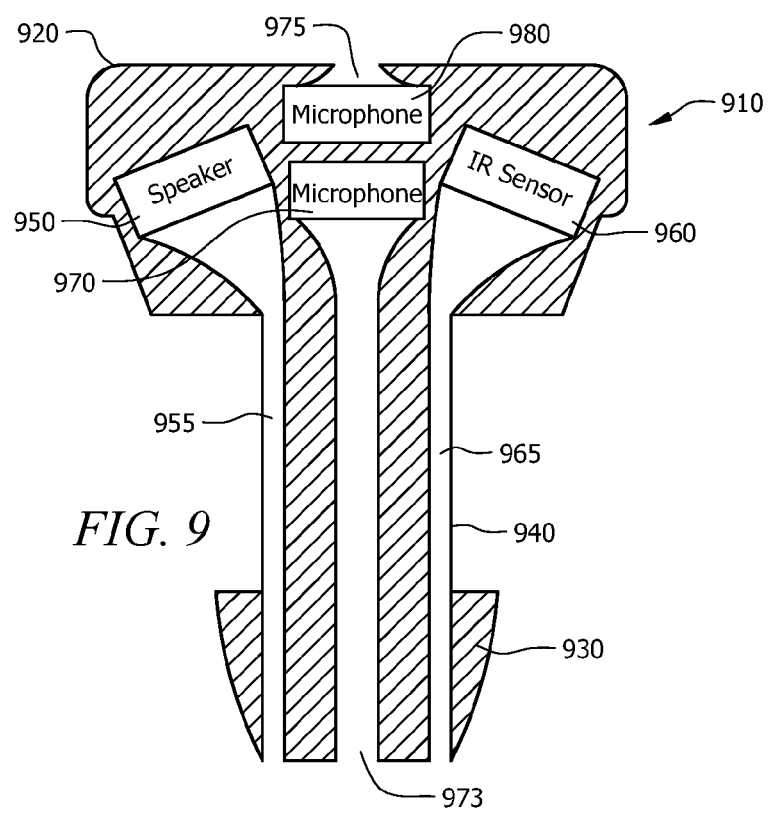
FIG. 9 illustrates a cross-sectional view of yet another embodiment of an in-ear headset device.

FIG. 9 shows an illustrative embodiment of an earpiece 910 of the sort that might be used for the QuietPro device. In FIG. 9, the main body housing 920 contains a plurality of electronic devices. For example, in FIG. 9, the main body comprises a speaker 950, an IR thermometry sensor 960, an inward facing microphone 970, and an outer facing microphone 980. One or more of these elements might be controlled by a controller, which might be incorporated into the earpiece, but also might be external as shown here. A sound tube 940 extends forward from the front of the main body 920 and has an ear tip 930 (typically for sealing the ear canal from sound and/or air infiltration and/or securing the earpiece in the ear canal) which is typically located at the front end of the sound tube 940. The sound tube or stem 940 of FIG. 9 may extend sufficiently in length so that when the earpiece is in place, the front of the sound tube extends past at least the first bend of the user's ear canal. Such deep insertion may provide for a better seal and/or may provide for better functionality of the electronics devices (for example, the IR sensor 960).

The outer facing microphone 980 typically has a rear (outward) transmission channel 975 and a rearward facing face, so that the outer microphone 980 can detect external sounds.

In some embodiments, such external sound may be passed through the earpiece in some situations by having the speaker 950 replicate the external sounds detected by the outer microphone 980. In other embodiments, the outer microphone 980 might be used with the speaker 950 to provide active noise cancelation (as an optional additional form of hearing protection). Since the rear transmission channel 975 is typically quite short, often no particular features are necessary. However, the rear transmission channel 975 could have at least an inner surface that is sound reflective in some embodiments (to aid in detection of external sound). The inward facing (inner) microphone 970 typically has a front (inner) transmission channel 973 and an inner (front) facing face, so that the inner microphone 970 may detect internal sounds (for example, sounds within the user's ear canal when the earpiece is in place sealing the ear canal). The inner transmission channel 973 may have an inner surface that is sound reflective in some embodiments, to aid in detection of sound within the ear canal in some embodiments by perhaps improving sensitivity of the readings. The inner transmission channel 973 typically runs the length of the sound tube 940, extending from about the face of the inner microphone 970 forward to the front of the sound tube 940. In some embodiments, the inner microphone 970 may be used pick up the user's voice when the user speaks (from within the ear canal, to allow for effective communication even in loud external noise environments), to work with the speaker to test the seal of the ear tip 930 (to see if the seal is effective or if the earpiece should be reinserted to ensure proper fit for a good seal), and/or to measure sound penetrating the EarTip (dosimetry, for example). See U.S. Pat. No. 6,728,385 or 6,567,524, for example, for additional details on such QuietPro features.

The speaker 950 of FIG. 9 has a sound waveguide 955 extending from about its face to the front of the sound tube 940. As in other embodiments, this sound waveguide 955 would typically be sound reflective. The IR sensor 960 of FIG. 9 has an IR waveguide 965 extending from about the face of the IR sensor 960 to the front of the sound tube 940. As in other embodiments, the IR waveguide 965 would typically be IR reflective. The waveguides would allow for the speaker and the IR sensor to operate effectively with the inner microphone even though the joint width of their front faces may be larger than the width of the sound tube 940 (since they allow for smaller passages). Additionally, the waveguides may allow for curvature, which may assist in positioning the electronic elements within the main body 920 and/or assist in overcoming issues relating to curvature in the ear canal (as the stem extends past at least the first bend in the ear canal, for example).

In some embodiments, a joint y-shaped waveguide might be used by the speaker 950 and the IR sensor 960, as discussed above for example. The sound waveguide 955 and the inner transmission channel 973 typically are separate and distinct (such that a single waveguide would not function for both the inner microphone and the speaker), since the speaker might interfere with the microphone's efforts to detect sound in the ear canal). In some embodiments, however, it might be possible to use a single waveguide for both purposes so long as they do not Operate simultaneously. And in some embodiments, the IR sensor waveguide 965 might join with the inner microphone transmission channel 973 by having a y-shaped passageway that is at least IR reflective (transmissive) and typically might be both IR and sound reflective. And as discussed earlier, the sound tube 940 and/or the waveguides (and perhaps the inner transmission channel) may be flexible so that they may accommodate the curvature of the user's ear canal when the earpiece is inserted into place for use (with the front end of the sound tube 940 typically extending past at least the first bend of the user's ear canal).

Figure 10:
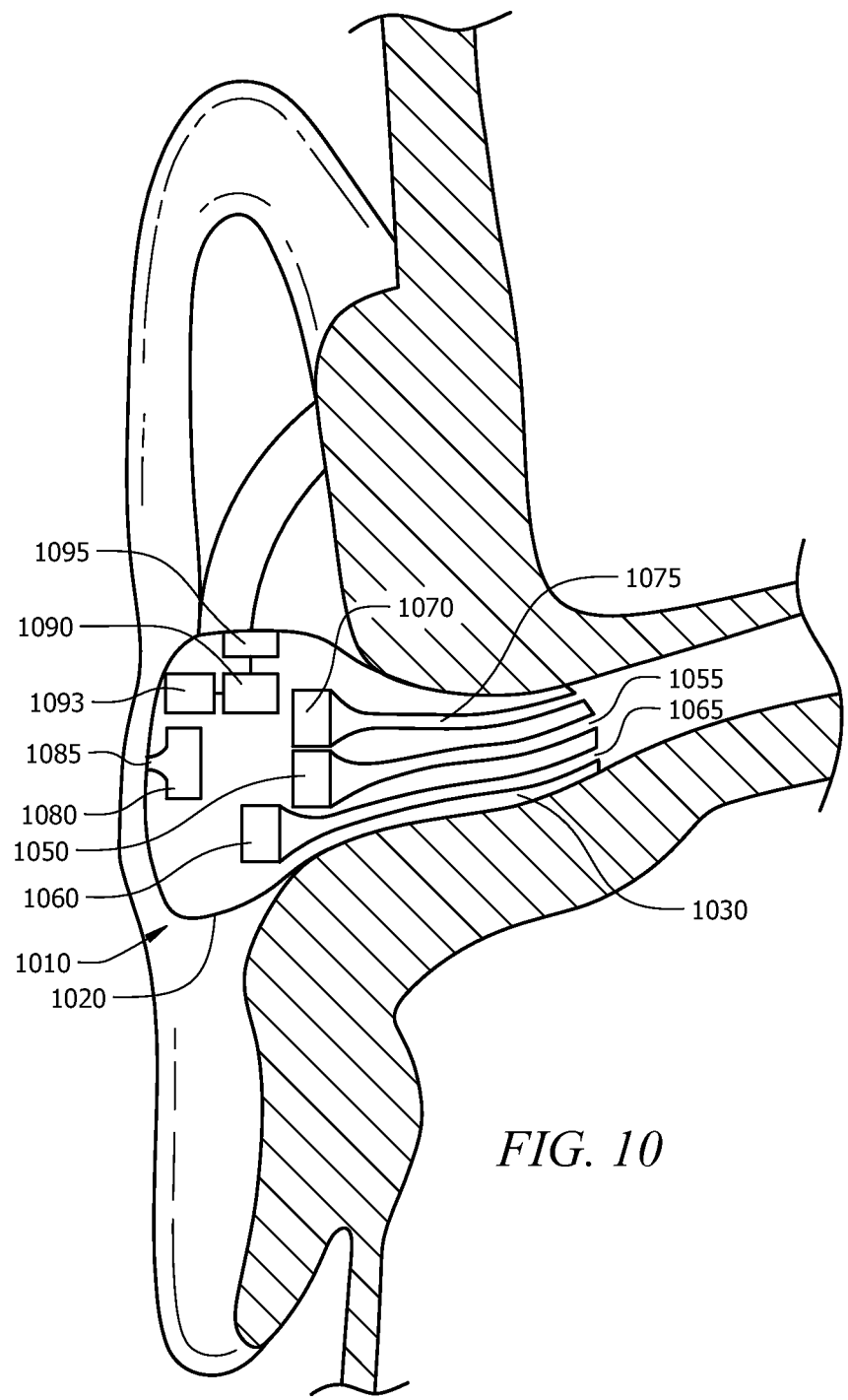
FIG. 10 illustrates a schematic of still another in-ear headset device.

FIG. 10 shows another illustrative embodiment of an earpiece of the sort that might be used for QuietPro. The embodiment of FIG. 10 has similar electronic components as discussed above with reference to FIG. 9, but it uses a unitary sealing element 1030 (typically shaped like a foam earplug) rather than a sound tube or stem with an ear tip. So, the earpiece 1010 comprises a main body 1020 and a sealing section 1030. The sealing section 1030 is designed to fit snuggly within a user's ear canal and to seal the ear canal from external noise. Typically, the sealing section 1030 comprises resilient foam and an outer shape to seal within an ear canal, and is sufficiently pliable and flexible to conform to the curvature of the user's ear canal. Typically the sealing section 1030 is sufficiently long to extend at least past the first bend in the user's ear canal. The main body 1020 typically sits within the bowl of the user's ear and houses several electronic elements. In FIG. 10, the main body 1020 comprises an outer microphone 1080 and often a rear transmission channel 1085 (allowing the outer microphone to effectively detect external sounds); a speaker 1050 (directed for transmission of sound into the user's ear canal past the sealing element, for example); an IR thermometry sensor 1060 (typically for sensing the temperature in the user's ear canal and/or tympanic membrane and often inward facing); and an inner microphone 1070 (typically for detecting sound within the user's ear canal). In some embodiments, the main body may also optionally comprise an electronics unit (for example, a processor) 1090, a power supply 1093, and/or a connection interface 1095. While one or more of these elements might be external to the earpiece, in FIG. 10 they are shown as being integral to the earpiece 1010 and located within the main body 1020.

In FIG. 10, a sound waveguide 1055 (allowing transmission of sound from the speaker 1050 into the user's ear canal toward the user's ear drum and/or tympanic membrane) extends from the face of the speaker 1050, through the sealing section 1030, to open into the user's ear canal at the front of the sealing section. An IR waveguide 1065 (allowing transmission of IR waves for detection of the temperature in the user's ear canal by the IR sensor) extends from the face of the IR sensor 1060, through the sealing section 1030, to open into the user's ear canal at the front of the sealing section. A front (inner) transmission channel 1075 (allowing transmission of sound from inside the user's ear canal to the inner microphone 1070), extends from the face of the inner microphone, through the sealing section 1030, to open in the user's ear canal at the front of the sealing section. So in FIG. 10 several passages (for example waveguides and/or transmission channels) typically extend through the sealing section 1030, allowing one or more of the electronic devices in the main body to interact with the ear canal when it is sealed by the sealing section. These passages through the sealing section typically should have sufficient rigidity to prevent the passages from collapsing upon themselves when the sealing section is inserted into a user's ear canal (so that they may stay open). In some embodiments, the passages might also be sufficiently flexible to allow for conformity to the curvature of the user's ear canal (although in other embodiments, the passages might be fairly rigid, and the pliability of the sealing section might serve to provide for conformity within the ear canal). Such flexibility may allow for deeper insertion, past at least the first bend.

Any of these embodiments might further incorporate additional or alternative physiological sensors. If multiple physiological sensors are included, then the temperature sensor typically would be the primary sensor, and any additional sensors would typically be secondary sensors used for verification (for example, to determine, false positives and/or false negatives). The controller would typically use the data provided by the one or more secondary physiological sensors to determine if a warning (for heat related illness for example) should be given. The warning might be monitored at a central station for several units, or the warning might be given to the user directly, via the speaker for example. In some embodiments, the controller (for example, a processor for the unit) would simply transmit the sensor data to an external processor for analysis and evaluation (typically using some form of wireless communication device). Alternatively, the controller might process the data locally and merely transmit a warning to an external processor and/or internally to the user. Local data processing would typically require less bandwidth, but external processing might allow for a smaller or less expensive controller unit. Typically, the warning given might be one or more simple binary signals (for example a green light means all clear and no problem, while a red light means danger; or an audible alarm means warning, and no alarm means all clear). Such simple warning may be useful in stressful situations (to reduce possible confusion) and/or may better protect the confidentiality of the user's physiological data (so that it could only be used for heat warnings, for example, and could not be used at some later date to evaluate the user's health or overall conditioning).

In some embodiments, the foam EarTip may be molded about the stem or sound tube. By way of example, an insert pour-molding process might be used. In an embodiment, the stem might be held in place in a section (typically the bottom) of the mold by a mandrel pin. The reaction materials might be added to the mold section and the other section (typically the top) of the mold might be closed. The foam of the EarTip might then form about the stem and/or other components.

In some embodiments, one or more physiological sensors might be incorporated into a wireless probe (like a pill-like device) that can be swallowed or otherwise located within the user's body. For example, a temperature sensor could be incorporated into a wireless pill device and swallowed, wirelessly radio transmitting temperature readings to a wireless receiver located within a PPE device (such as a helmet, in-ear device, or armband). The PPE device might also include one or more sensors for detecting secondary physiological readings. Such embodiments might then sense the user's physiological condition (and optionally use secondary physiological readings as a check), for example to monitor for potential heat-related illness.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A device comprising:
   an earpiece for use in a user's ear having a sealing ear tip;
   at least one temperature sensor;
   a speaker having a face;
   and or more waveguides;
   wherein:
      the earpiece has sufficient length and flexibility so that when in place in the user's ear it comfortably extends forward past at least a first bend of the user's ear canal;

the sealing tip is sufficiently pliable to form a good seal in the user's ear canal;

the temperature sensor comprises an IR sensor having a face, and the one or more waveguides comprise an IR waveguide;

the IR waveguide comprises an elongate hollow tube having an inner surface that is substantially reflective of IR which extends from the face of the IR sensor forward so that, when in place in the user's ear, the IR waveguide allows the IR sensor to detect temperature in the ear canal;

the one or more waveguides further comprise a sound waveguide;

the sound waveguide comprises an elongate hollow tube extending from the speaker face forward so that, when in place in the user's ear, the sound waveguide directs sound produced by the speaker into the user's ear canal at a point past the sealing ear tip;

the sound waveguide comprises an inner surface that is substantially sound reflective;

the sound waveguide and the IR waveguide are separate and apart waveguides offset side-by-side;

the earpiece further comprises a main body, for housing the speaker and the temperature sensor, and a stem; wherein:

the stem is elongate and has a front and a rear;

the rear of the stem is securely attached to the main body; and the one or more waveguides span the length of the stem;

the speaker is laterally offset from the stem, with the speaker face angled with respect to a centerline of the stem so that the speaker face is not directly pointed towards the stem along a line parallel to the centerline of the stem;

the temperature sensor is laterally offset from the stem, with the temperature sensor face angled with respect to a centerline of the stem so that the temperature sensor face is not directly pointed towards the stem along a line parallel to the centerline of the stem; and the IR waveguide and the sound waveguide extend essentially parallel to each other for most of their lengths, with only a rear portion of the sound waveguide curving to orient with the angled, offset face of the speaker and only a rear portion of the IR waveguide curving to orient with the angled, offset face of the temperature sensor.

2. The device of claim 1 wherein:

the main body is shaped to fit in the bowl of the user's ear;

the IR waveguide and the sound waveguide each comprise at least one curve; and the waveguides function despite any additional curvature arising when the earpiece is inserted into the user's ear canal.

3. The device of claim 1 wherein the IR waveguide comprises a mirrored inner surface of polished metal.

4. The device of claim 1 wherein the temperature sensor comprises a thermistor; and the ear tip comprises polyurethane foam.

5. The device of claim 1 wherein the IR waveguide comprises a fiber-optic cable.

6. The device of claim 1 further comprising at least one secondary physiological sensor for verification of heat related illness detected by the temperature sensor.

7. The device of claim 6 further comprising a controller, wherein the controller uses the secondary physiological sensor as verification of the temperature sensor to determine heat-related illness designation.

8. The device of claim 7 wherein the controller wirelessly transmits notification of warning to an external processor.

9. The device of claim 1 wherein the sealing ear tip comprises polyurethane foam and is securely attached about the front of the stem; and wherein a rear of the foam ear tip comprises an integral rear flange skirt, extending rearward to form a foam skirt periphery encompassing a rear annular space.

10. The device of claim 1 wherein:

the sound waveguide comprises an inner surface that is substantially sound reflective to transmit sound the length of the sound waveguide with less than about 6 dB attenuation; and the IR waveguide comprises an elongate hollow tube having an inner surface that is substantially reflective for spectrally flat transmission of IR which extends from the face of the IR sensor forward so that, when in place in the user's ear, the IR waveguide allows the IR sensor to be aligned to detect the temperature of the user's tympanic membrane.

11. The device of claim 1 wherein the stem is sufficiently flexible to comfortably conform to curvature of the user's ear canal, but sufficiently stiff to allow for effective deep insertion, with a hardness of 65-85 Shore A.

12. The device of claim 1 wherein a joint width of the face of the speaker and the face of the temperature sensor is larger than a width of the stem.

13. The device of claim 1 wherein the earpiece has sufficient length and flexibility so that when in place in the user's ear it comfortably extends forward past a second bend of the user's ear canal.

14. The device of claim 1 wherein the main body further houses an inward facing microphone and an outward facing microphone, and wherein the device further comprises an inner transmission channel with an inner surface that is sound reflective and which extends from the inward facing microphone, through the length of the stem, forward to the front of the stem.

* * * * *